United States Patent
Smith et al.

(10) Patent No.: US 12,043,587 B2
(45) Date of Patent: Jul. 23, 2024

(54) SIMULTANEOUS DEHYDRATION, OLIGOMERIZATION, AND CRACKING OF C2-C5 ALCOHOLS

(71) Applicant: Gevo, Inc., Englewood, CO (US)

(72) Inventors: Jonathan Smith, Highlands Ranch, CO (US); Madeline Sjodin, Englewood, CO (US)

(73) Assignee: Gevo, Inc., Englewood, CO (US)

( * ) Notice: Subject to any disclaimer, the term of this patent is extended or adjusted under 35 U.S.C. 154(b) by 58 days.

(21) Appl. No.: 17/695,993

(22) Filed: Mar. 16, 2022

(65) Prior Publication Data

US 2022/0227685 A1 Jul. 21, 2022

Related U.S. Application Data

(63) Continuation of application No. PCT/US2020/053312, filed on Sep. 29, 2020.

(60) Provisional application No. 62/908,457, filed on Sep. 30, 2019, provisional application No. 62/910,948, filed on Oct. 4, 2019, provisional application No. 62/914,837, filed on Oct. 14, 2019, provisional application No. 62/938,172, filed on Nov. 20, 2019.

(51) Int. Cl.

| | |
|---|---|
| C07C 1/24 | (2006.01) |
| B01J 21/04 | (2006.01) |
| B01J 21/06 | (2006.01) |
| B01J 21/08 | (2006.01) |
| B01J 23/30 | (2006.01) |
| B01J 29/40 | (2006.01) |
| C07C 2/12 | (2006.01) |
| C07C 6/04 | (2006.01) |
| C10G 3/00 | (2006.01) |

(52) U.S. Cl.
CPC ............... *C07C 1/24* (2013.01); *B01J 21/04* (2013.01); *B01J 21/066* (2013.01); *B01J 21/08* (2013.01); *B01J 23/30* (2013.01); *B01J 29/40* (2013.01); *C07C 2/12* (2013.01); *C07C 6/04* (2013.01); *C10G 3/49* (2013.01); *C07C 2521/04* (2013.01); *C07C 2521/06* (2013.01); *C07C 2521/08* (2013.01); *C07C 2523/30* (2013.01); *C07C 2529/40* (2013.01); *C10G 2400/20* (2013.01); *C10G 2400/22* (2013.01)

(58) Field of Classification Search
CPC .... C07C 1/20; C07C 2/12; C07C 6/04; C10G 3/00
See application file for complete search history.

(56) References Cited

U.S. PATENT DOCUMENTS

| | | | |
|---|---|---|---|
| 4,049,573 A * | 9/1977 | Kaeding | B01J 29/40 502/77 |
| 4,302,357 A | 11/1981 | Kojima et al. | |
| 4,590,320 A | 5/1986 | Sapre | |
| 7,371,916 B1 | 5/2008 | Kalnes et al. | |
| 8,378,136 B2 | 2/2013 | Dubois | |
| 8,450,543 B2 * | 5/2013 | Peters | C07C 45/28 585/314 |
| 8,552,241 B2 | 10/2013 | Coupard et al. | |
| 9,840,676 B1 | 12/2017 | Harvey | |
| 10,201,806 B2 | 2/2019 | Braunsmann et al. | |
| 2011/0213174 A1 | 9/2011 | Dubois | |
| 2016/0310934 A1 | 10/2016 | Braunsmann et al. | |
| 2017/0137357 A1 | 5/2017 | Hu et al. | |
| 2023/0065667 A1 | 3/2023 | Smith et al. | |

FOREIGN PATENT DOCUMENTS

| | | | | |
|---|---|---|---|---|
| CN | 101172920 A | 5/2008 | | |
| CN | 101304963 A | 11/2008 | | |
| CN | 103140458 A | 6/2013 | | |
| CN | 103274884 A | 9/2013 | | |
| CN | 107312569 A | 11/2017 | | |
| EP | 2374780 A1 | 10/2011 | | |
| EP | 2547639 B1 * | 8/2016 | ............. | B01J 21/04 |
| EP | 2547639 B1 | 8/2016 | | |
| WO | 2006036293 A1 | 4/2006 | | |

(Continued)

OTHER PUBLICATIONS

International Search Report And Written Opinion received for PCT Patent Application No. PCT/US2020/053312, mailed on Jan. 6, 2021, 12 pages.

Sadeghpour et al. "High-Temperature Efficient Isomorphous Substitution of Boron Into 32,64 Zsm-5 Nanostructure For Selective And Stable Production of Ethylene And Propylene From Methanol", Materials Chemistry and Physics, 217(1):133-150 (Sep. 15, 2018) (3 pages).

International Search Report and Written Opinion received for PCT Application No. PCT/US2022/026042, mailed on Nov. 3, 2022, 20 pages.

(Continued)

*Primary Examiner* — Sharon Pregler
(74) *Attorney, Agent, or Firm* — Mintz, Levin, Cohn, Ferris, Glovsky and Popeo, P.C.

(57) ABSTRACT

This disclosure relates to a single stage process for the direct conversion of alcohols, e.g. ethanol, to olefinic mixtures ($C_2$-$C_7$) with low levels of aromatics carried out in a single reactor with two fixed catalyst beds in series, or two catalytic fixed bed reactors in series wherein the first reactor operates at a lower or higher temperature than the operating temperature of the second reactor. The process transformation of ethanol is comprised of ethanol dehydration to ethylene and water in high yield with the first catalyst in the first reactor, or via the first fixed catalyst bed, followed by directly feeding the ethylene and water to the second reactor, or second fixed catalyst bed, with conversion of said ethylene and water to a $C_2$-$C_7$ olefinic mixture with the second catalyst(s) in high yields with minimal aromatic compound formation.

22 Claims, No Drawings

(56) References Cited

FOREIGN PATENT DOCUMENTS

| WO | 2010097175 A1 | 9/2010 |
| WO | 2011085223 A1 | 7/2011 |
| WO | 2011113834 A1 | 9/2011 |
| WO | 2011113836 A1 | 9/2011 |
| WO | 2011161045 A1 | 12/2011 |
| WO | 2015088707 A1 | 6/2015 |
| WO | 2018071905 A1 | 4/2018 |
| WO | 2019136283 A1 | 7/2019 |
| WO | 2021067294 A1 | 4/2021 |
| WO | 2022226371 A2 | 10/2022 |

OTHER PUBLICATIONS

Invitation to Pay Additional Fees received for Application No. PCT/US2022/026042, mailed on Aug. 5, 2022, 11 pages.
Strizhak et al. (Nov. 15, 2017) "Methanol Conversion to Olefins on H-ZSM-5/Al2O3 Catalysts: Kinetic Modeling", Reaction Kinetics, Mechanisms and Catalysis, 123(1):247-268.

* cited by examiner

SIMULTANEOUS DEHYDRATION, OLIGOMERIZATION, AND CRACKING OF C2-C5 ALCOHOLS

CROSS-REFERENCE TO RELATED APPLICATIONS

This application is a continuation application, filed under 35 U.S.C. § 120, of PCT International Patent Application No. PCT/US2020/053312 with an International Filing Date of Apr. 8, 2021, and entitled "Simultaneous Dehydration, Dimerization, and Metathesis of C2-C5 Alcohols" which claims priority to and the benefit of U.S. Provisional Patent Application Ser. No. 62/908,457, filed on Sep. 30, 2019, entitled "Simultaneous Dehydration, Dimerization, Metathesis, and Oligomerization of C2-C5 Alcohols"; U.S. Provisional Patent Application Ser. No. 62/910,948, filed on Oct. 4, 2019, entitled "Simultaneous Dehydration, Dimerization, Metathesis, and Oligomerization of C2-C5 Alcohols"; U.S. Provisional Patent Application Ser. No. 62/914,837, filed on Oct. 14, 2019, entitled "Simultaneous Dehydration, Dimerization, Metathesis, and Oligomerization of C2-C5 Alcohols"; and U.S. Provisional Patent Application Ser. No. 62/938,172, filed on Nov. 20, 2019, entitled "Simultaneous Dehydration, Dimerization, Metathesis, and Oligomerization of C2-C5 Alcohols"; each of which are incorporated by reference in its entirety for all purposes.

TECHNICAL FIELD

The subject matter described herein relates to a process for converting one or more $C_2$-$C_5$ linear or branched alcohols to one or more $C_2$-$C_7$ olefins. The one or more $C_2$-$C_5$ alcohols can be from bio-based processes. The process can be performed with two reactors in series, or in one reactor with two catalyst beds. The $C_2$-$C_7$ olefins are suitable for oligomerization and conversion into gasoline, jet, and/or diesel fuels.

BACKGROUND

There is an increasing demand for the use of biomass sources for replacing petroleum as the starting point for the synthesis of fuels. The use of biomass-derived alcohols for the synthesis of base stocks for fuels is therefore of great interest. The reactions for converting alcohols to a base stock for fuels typically start with dehydration followed by olefin oligomerization. $C_2$-$C_5$ alcohols are traditionally dehydrated in a single unit operation, at between 300-500° C. in the presence of a dehydration catalyst, resulting in production of the $C_2$-$C_5$ olefin along with water. The water is removed, and the $C_2$-$C_5$ olefin is further processed/purified to remove unreacted $C_2$-$C_5$ alcohols and/or impurities prior to conversion to chemicals and/or fuels. Relative to ethanol ($C_2$ alcohol), the traditional approach to conversion to chemicals and/or fuels utilizes discrete unit operations to accomplish i) dehydration to ethylene, ii) ethylene purification followed by dimerization to butenes, iii) metathesis to propylene, iv) oligomerization of butenes to unsaturated Jet and/or Diesel fuel precursors, or v) direct oligomerization of ethylene to unsaturated Jet and/or Diesel fuel precursors. Similarly, the approach to converting $C_4$ or $C_5$ alcohols to chemicals and/or fuels utilize discrete unit operations to accomplish i) dehydration to the $C_4$ or $C_5$ olefin, ii) olefin purification to remove oxygenates and/or unreacted alcohols, and iii) oligomerization to unsaturated Jet and/or Diesel fuel precursors. Efforts have been made to convert alcohols into fuel stocks as described below.

International patent application WO2010/097175A1 relates to the direct conversion of oxygenated compounds to liquid hydrocarbons with a low aromatic content. The process may be carried out via a two-stage process in which both the first and second stage reactors in series both reactors use zeolite catalysts. Methanol single pass conversion is typically >95% and the reported final liquid product mainly consists of 60-85% $C_n$ olefins with n≥5, between 15-40% by weight of light $C_n$ olefins with n=2-4, and <10% aromatics. The final liquid product is hydrogenated to give gasoline cuts, or oligomerized according to conventional processes to give mixtures of gasoline, kerosene, and diesel. However, the examples describe methanol, which is more toxic than ethanol, and no examples are given with ethanol as feed. Further, the major products are higher carbon olefins (n>5) instead of light carbon (2<n<4) olefins, which may be the result of using zeolite type catalysts in both reactors.

U.S. Pat. No. 8,552,241 relates to a method for converting ethanol in a single step to a diesel fuel base stock which comprises contacting ethanol with an acid catalyst at a reaction temperature of 300-500° C. The catalyst used is a 50/50 mixture of a γ-alumina in combination with a commercial Axens catalyst 'type IS463' marketed as an alumina-based catalyst for skeletal isomerization of $C_4$ and $C_5$ olefin cuts. Only one reactor and only one catalyst type is used. The typical single pass product distribution consisted of a hydrocarbon fraction of 40-50%, and an organic liquid phase yield of 5-20%. The organic liquid phase consists of ~50% olefins of which $C_6$ olefins are the majority, and ~40% has a boiling point above 150° C., and therefore compatible with the diesel pool. The 40-50% hydrocarbon gaseous phase predominately contains ethylene and ethane as well as traces of $C_1$, $C_3$, $C_4$ and $C_5$. In this case, the yield to the organic liquid phase is relatively low with ~20% having a boiling point above 150° C. The other 80% of the organic liquid and hydrocarbon fraction is a predominately ethylene and ethane as well as traces of $C_1$, $C_3$, $C_4$ and $C_5$ and $C_6$ olefins. Thus, the process described are not efficient or economical.

U.S. Pat. No. 9,840,676 relates to a method for converting ethanol in a three-step process into fuels which can be utilized as full performance or military jet or diesel fuels. The process begins with ethylene formation followed by trimerization to form hexenes and finally oligomerization to jet and diesel fractions. The multistage process converts ethanol into lower carbon olefins, such as $C_2$-$C_4$ olefins, then requires further oligomerization to produce fuels such as gasoline and diesel. The catalysts used in trimerization of ethylene to hexenes were Ziegler Natta catalysts.

In traditional ethanol dehydration processes, ethanol conversion is nearly complete. The increase of $C_2$-selectivity while keeping a high ethanol conversion is of importance to gain in process efficiency and to save expensive steps of downstream separation/purification. The reaction products are then mainly water and ethylene. The ethylene being obtained with selectivity as high as 96%. The subsequent oligomerization of ethylene requires high gauge pressures, generally ranging between 2-4 MPa, but lower temperatures, generally between 20-200° C. However, the direct oligomerization of ethylene results in relatively low amounts (~40% highest reported level) of $C_{10+}$ or diesel fraction.

SUMMARY

Aspects of the current subject matter relate inter alia to processes for converting $C_2$-$C_5$ alcohols to $C_2$-$C_7$ olefins.

Consistent with some aspects of the current subject matter, a processes for converting one or more $C_2$-$C_5$ linear or branched alcohols to one or more $C_2$-$C_7$ olefins is disclosed. The process includes two different catalyst systems either using either two reactors in series wherein one catalyst is in each reactor, or one reactor with two catalyst beds. For processes which use two reactors in series, the water product from the first reactor can be separated from the stream before entering the second reactor, or left in the stream.

In variations, one or more of the following features may be included in any feasible combination. For example, the one or more $C_2$-$C_5$ linear or branched alcohols can be $C_2$-$C_4$ linear or branched alcohols. The one or more $C_2$-$C_7$ olefins formed by the processes described herein can be $C_2$-$C_6$ olefins. Further, the mass yield of the one or more $C_2$-$C_7$ olefins can be between 70% to 99%.

The temperature, pressure, and WHSV of processes which occur in two reactors in series can be different between the two reactors, or the same. For example, the temperature of the first reactor can be from 300° C. to 450° C. including all the subranges in between, and the temperature of the second reactor can be from 320° C. to 450° C. including all the subranges in between. The gauge pressure of the first reactor and second reactors can independently be from 0 to 10 bar including all the subranges in between. The WHSV of the first reactor and second reactor are each independently from 0.5 to 10 and all the subranges in between.

In processes which occur in one reactor with two catalyst beds, the temperature, pressure, and WHSV are consistent as the feed stream passes from the first catalyst bed to the second catalyst bed. The temperature of the one reactor processes can be from 300° C. to 400° C. including all the subranges in between. The pressure can be from 0 to 10 bar including all subranges in between. The WHSV can be from 0.5 to 10 and all the subranges in between.

The processes described herein comprise two catalyst systems regardless of whether the reaction is performed in one or two reactors. The first catalyst comprises $\gamma$-alumina catalyst, which can comprise Zr. The first catalyst may not comprise a zeolite catalyst. The second catalyst comprises zeolite catalyst which comprises boron, phosphorus, or both. The second catalyst can also include $\gamma$-alumina catalyst, W—$SiO_2$ catalyst, or W—Zr catalyst, wherein the $\gamma$-alumina optionally includes Zr, W, or Mo.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

DETAILED DESCRIPTION

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Reference throughout this specification to "one embodiment" or "an embodiment" means a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The word "about" when immediately preceding a numerical value means a range of plus or minus 10% of that value, e.g., "about 50" means 45 to 55, "about 25,000" means 22,500 to 27,500, etc. Furthermore, the phrases "less than about" a value or "greater than about" a value should be understood in view of the definition of the term "about" provided herein.

"Oxygenate" refers to compounds which include oxygen in their chemical structure. Examples of oxygenates include, but are not limited to water, alcohols, esters, and ethers.

"WHSV" refers to weight hourly space velocity and is defined as the weight of the feed flowing per unit weight of the catalyst per hour.

"Single stage transformation" refers to processes which occur within a single reactor system.

All yields and conversions described herein are on a mass basis unless specified otherwise.

Described herein are processes to convert alcohols in a single-stage reactor with dual catalysts, or in a two-stage reactor configuration (in series) with separate catalyst beds. The alcohols are converted to an olefinic mixture comprised of primarily $C_3$-$C_7$ olefins with low levels of aromatic compounds. The processes provide paths towards economical ways to convert alcohols, e.g. ethanol, to base stocks for the production of fuels. Further, the processes described herein can be performed at lower pressures and higher temperatures with higher yields of olefins in comparison to previous reports. The processes comprise a single stage transformation of an aqueous bioalcohol feedstock derived from biomass into a higher molecular weight olefinic mixture, which can easily be oligomerized in high yield to $C_{10+}$ hydrocarbons or diesel fractions. The single-stage reactor or two-stage reactor configurations use specific catalytic systems, which make it possible to minimize the production of aromatic compounds and therefore maximize production of middle distillates. This constitutes both an asset for the ethanol refiner and an advantage from the standpoint of lasting development. Processes described herein convert $C_2$-$C_5$ alcohols efficiently and economically as a base stock for fuels. Conversion of $C_2$-$C_5$ alcohols to the desired fuel product precursors (i.e. $C_3$-$C_7$ olefins) in high yields reduces processing costs.

Simultaneously dehydrating/dimerizing/metathesizing a $C_2$-$C_5$ alcohol in one reactor is challenging due to higher temperatures required for complete dehydration (300-500°

C.), and large amounts of water present. Implementation of a single unit operation capable of simultaneously dehydrating, dimerizing, and metathesizing an alcohol requires that catalysts employed be able to withstand high temperatures along with large amounts of water and other oxygenates. The ability to accomplish numerous unit operations and chemical transformations in a single stage provides favorable economics due to reduced fixed and variable costs, lower capital investment, and increased productivity.

Aspects of the currently subject matter overcome challenges by providing processes in which a two-catalyst system is used to convert $C_2$-$C_5$ linear or branched alcohols to $C_2$-$C_7$ olefins in high yield with low levels of aromatics at competitive costs. The $C_2$-$C_7$ olefins can be easily oligomerized to base stocks used in the production of fuels in high yields. The process can be carried out in two catalytic fixed bed reactors in series wherein the first reactor operates at a lower or higher temperature than the operating temperature of the second reactor. The process is comprised of the steps of alcohol dehydration to lower carbon chain olefins and water in high yields using a first catalyst in the first reactor, followed by directly feeding the lower carbon chain olefins and water to the second reactor with conversion of said lower carbon chain olefins and water to a $C_2$-$C_7$ olefinic mixture using a second catalyst. Furthermore, in the two-stage process, the water formed during dehydration of alcohols within the first reactor having the first catalyst may be separated from the lower carbon chain olefins after exiting the first reactor prior to feeding into the second reactor including the second catalyst. Alternatively, alcohols, e.g. ethanol, may be converted to olefinic mixtures ($C_2$-$C_7$) in a single reactor having the first catalyst in the top section of the reactor with the second catalyst being located in a section of the reactor below the first catalyst. In either the two-stage or single-stage processes, the resulting $C_2$-$C_7$ olefinic mixture is suitable for oligomerization into either gasoline, jet, or diesel fuel cuts at relatively low temperatures and pressures depending upon the oligomerization catalyst selected.

One advantage of having the two catalyst beds in two reactors in series, rather than in one reactor, is that it allows for the capability and flexibility to operate the reactors at two different reaction temperatures. In this process, the effluent from the first dehydration reactor, with water vapor and other minor impurities, is directed 'as-is' to the second reactor in series at an optimum temperature depending upon the target fuel and/or olefinic mixture. For example, dehydration of ethanol to ethylene at 360° C., over silicated, zirconated, titanated, niobium, or fluorinated $\gamma$-alumina in the first reactor (fixed bed 'A'), followed by directing the gaseous non-condensed ethylene enriched stream including water and impurities to the second reactor (fixed bed 13') packed with i) a metathesis catalyst (i.e. tungstated alumina, etc.) admixed with a ZSM-5 zeolite or doped ZSM-5 zeolite, or ii) a doped ZSM-5 zeolite admixed with a zirconated alumina catalyst at an internal temperature between 300-500° C. and at pressures between 0-30 bar and WHSV 0.5-10, accomplishes ethylene dimerization and metathesis to $C_3$-$C_7$ olefins in high yields. This two-reactor in series approach enables the practitioner to optimize reactor temperatures independently and allows catalyst regeneration of the second reactor (fixed bed 13') without disrupting operation of the first reactor (fixed bed 'A').

Disclosed herein is a process for converting one or more $C_2$-$C_5$ linear or branched alcohols to one or more $C_2$-$C_7$ olefins, the process comprising contacting a first stream comprising the $C_2$-$C_5$ linear or branched alcohols with a first catalyst in a first reactor at a temperature from 200° C. to 500° C., a gauge pressure from 0 to 30 bar, and a WHSV of at least 0.5, wherein the first catalyst comprises an alumina catalyst including one or more of Si, Zr, Ti, Nb, W or F in neutral or ionic form, to form a second stream; and contacting the second stream with a second catalyst in a second reactor at a temperature from 200° C. to 500° C., gauge pressure from 0 to 30 bar, and a WHSV of at least 0.5, wherein the second catalyst comprises a doped or undoped zeolite catalyst and/or a doped or undoped W—Zr catalyst and forming the one or more $C_2$-$C_7$ olefins in a mass yield of at least 65%.

An alternative two-reactor scenario can be advantageous for conversion of ethanol into $C_3$-$C_7$ olefins in high yield. For example, dehydration of ethanol to ethylene at 360° C., over silicated, zirconated, titanated, niobium, or fluorinated $\gamma$-alumina in the first reactor (fixed bed 'A') followed by water removal and directing the gaseous non-condensed ethylene enriched stream, saturated with water, to the second reactor (fixed bed 13) packed with i) a metathesis catalyst (i.e. tungstated alumina, etc.) admixed with a ZSM-5 zeolite or doped ZSM-5 zeolite, or ii) a doped ZSM-5 zeolite admixed with a zirconated alumina catalyst at an internal temperature between 300-500° C. and at gauge pressures between 0-30 bar and WHSV 0.5-10 accomplishes ethylene dimerization and metathesis to C3-C7 olefins in high yield. This two-reactor in series approach enables the practitioner to optimize reactor temperatures independently, allows catalyst regeneration of the second reactor (fixed bed 'B') without disrupting operation of the first reactor (fixed bed 'A'), and enables the use of catalyst combinations that exhibit less stability to the presence of large amounts of water.

The present disclosure also provides a process for converting one or more $C_2$-$C_5$ linear or branched alcohols to one or more $C_2$-$C_7$ olefins, the process comprising: contacting a first stream comprising the $C_2$-$C_5$ linear or branched alcohols with a first catalyst in a first reactor at a temperature from 200° C. to 500° C., a gauge pressure from 0 to 30 bar, and a WHSV of at least 0.5, wherein the first catalyst comprises an alumina catalyst including one or more of Si, Zr, Ti, Nb, W or F in neutral or ionic form, to form a second stream; separating a portion of water from the second stream; and contacting the second stream with a second catalyst in a second reactor at a temperature from 200° C. to 500° C., a gauge pressure from 0 to 30 bar, and a WHSV of at least 0.5, wherein the second reactor comprises a doped or undoped zeolite catalyst and/or a doped or undoped W—Zr catalyst and forming the one or more $C_2$-$C_7$ olefins in a mass yield of at least 70%.

A single unit operation (i.e. a single reactor), can also be used to convert lower alcohols into a viable feedstock of higher molecular weight olefins in high yield, which can be easily oligomerized to base stocks for fuels in high yield. For example, passing a vaporized stream of undenatured fuel grade (>92.1% v/v ethanol/water) or hydrous ethanol over fixed catalyst bed 'A' containing silicated, zirconated, titanated, niobium, or fluorinated $\gamma$-alumina at between 300-400° C. at gauge pressures between 0-30 bar and a WHSV between 0.5-10, followed by directly passing the ethylene vapor stream without isolation, purification, or removal of water over fixed catalyst bed 'B' in the same reactor containing; i) a doped or undoped tungstated zirconium catalyst, or ii) a tungstated, molybdenumated, silicated or zirconated alumina admixed with a doped or undoped ZSM-5 zeolite catalyst, at the same temperature and gauge pressures (i.e. 300-400° C., 0-30 bar) provides the ethanol producer with a $C_3$-$C_7$ olefinic mixture in high yields with minimal aromatic content. The $C_3$-$C_7$ olefinic mixture can be separated for sale, or after removal of condensed water, oligomerized 'as-is' to primarily jet and/or diesel fuels in high yields.

This disclosure also describes a process for converting one or more $C_2$-$C_5$ linear or branched alcohols to one or more $C_2$-$C_7$ olefins, the process comprising contacting a first stream comprising the $C_2$-$C_5$ linear or branched alcohols with a first catalyst bed in a reactor at a temperature from 200° C. to 500° C., a gauge pressure from 0 to 30 bar, and a WHSV of at least 0.5, wherein the first catalyst bed comprises an alumina catalyst including one or more of Si, Zr, Ti, Nb, W or F in neutral or ionic form, to form a second stream; and contacting the second stream with a second catalyst bed in the reactor at the same temperature, pressure, and WHSV as the first reactor, wherein the second catalyst bed comprises a doped or undoped zeolite catalyst and/or a doped or undoped W—Zr catalyst and forming the one or more $C_2$-$C_7$ olefins in a mass yield of at least 70%.

The $C_2$-$C_5$ linear or branched alcohols useful in the present disclosure includes any $C_2$-$C_5$ linear or branched alcohol known by one of skill in the art. For example the $C_2$-$C_5$ alcohols can be one or more of ethanol, propanol, iso-propanol, 1-butanol, isobutanol, 2-butanol, tert-butanol, pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol. The $C_2$-$C_5$ alcohols of the present invention can be from bio-based processes, such as, but not limited to, fermentation. For example, the $C_2$-$C_5$ linear or branched alcohols are bio-based and produced by fermentative processes. The $C_2$-$C_5$ linear or branched alcohols are not derived from petroleum.

Consistent with some aspects of the subject matter, the one or more $C_2$-$C_5$ linear or branched alcohols is ethanol, propanol, isopropanol, 1-butanol, isobutanol, 2-butanol, or tert-butanol. In many instances, the one or more $C_2$-$C_5$ linear or branched alcohols is ethanol, propanol, butanol, or a combination thereof. For example, the one or more $C_2$-$C_5$ linear or branched alcohols is ethanol. In another example, the one or more $C_2$-$C_5$ linear or branched alcohols is isobutanol.

Consistent with some aspects of the subject matter, the one or more $C_2$-$C_7$ olefins of any processes described herein are any suitable olefin. In many instances the one or more $C_2$-$C_7$ olefins is one or more $C_2$-$C_6$ olefins. In some examples, the one or more $C_2$-$C_7$ olefins includes ethylene, propylene, butenes, $C_5$-$C_6$ olefins, or a combination thereof.

The temperature for the processes described herein can be any suitable reactor temperature known by one of skill in the art. In the processes comprising two reactors, the temperature of the first reactor can be higher, lower, or the same as the second reactor. In some instances, the temperature of the first reactor is from 300° C. to 450° C. In some examples, the temperature of the first reactor is from 300° C. to 420° C. For example the temperature of the first reactor is about 360° C.

In some examples, the temperature of the second reactor is from 320° C. to 420° C. For example the temperature of the second reactor is from 340° C. to 400° C. In some examples, the temperature of the second reactor is from 350° C. to 450° C. For example, the temperature of the second reactor is from 380° C. to 410° C.

In the processes comprising one reactor with two catalyst beds, the temperature of the reactor can be any suitable temperature. The temperature is from 300° C. to 400° C. For example, the temperature is about from 330° C. to 360° C.

The gauge pressure for the processes described herein can be any suitable gauge pressure known by one of skill in the art. In the processes comprising two reactors, the gauge pressure of the first reactor can be higher, lower, or the same as the second reactor. In some instances, the gauge pressure of the first reactor and second reactor are each independently from 0 to 30 bar. In some instances the gauge pressure of the first reactor and second reactor are each independently from 0 to 10 bar. For example, the gauge pressure of the first reactor and second reactor are each independently 0 to 1 bar. In some examples, the gauge pressure of the first reactor and second reactor are each independently 0 bar.

The WHSV for the processes described herein can be any suitable WHSV known by one of skill in the art. In the processes comprising two reactors, the WHSV are each independently at least 0.5. In many instances, the WHSV of the first and second reactors are each independently from 0.5 to 10. For example, the WHSV of the first and second reactors are each independently from 0.5 to 5. In some examples, the WHSV of the first and second reactors are each independently at least 1. In some examples, the WHSV of the first and second reactors are each about 2.1.

In the processes comprising one reactor with two catalyst beds, the WHSV can be from 0.5 to 10. In some examples, the WHSV is at least 1. In some examples, the WHSV is from 2.1 to 2.3.

Granular or extruded catalysts are suitable for the reactions even though no specific size and morphology are mandatory. Catalysts with a size greater than 0.1 mm are more suitable, and the size of 0.4-1.0 mm is most suitable for the operability and pressure drop.

The first catalyst comprises an alumina catalyst including Si, Zr, Ti, Nb, W or F (i.e. a doped alumina catalyst) disclosed herein are more stable in the present process as compared to standard commercial grade alumina catalysts. Consistent with some aspects of the subject matter, the first catalyst comprises an alumina catalyst including one or more of Si (silicon), Zr (zirconium), Ti (titanium), Nb (niobium), W (tungsten) or F (fluorine). One or more of Si, Zr, Ti, Nb, W or F can be in an ionic form. In some instances, the alumina catalyst comprises the Zr. The Zr can be zirconium (IV). The first catalyst may not comprise a zeolite catalyst.

Zr can be present in an amount from 2 wt. % to 10 wt. % in the first catalyst. In some examples, Zr is present in an amount of about 4.0 wt. % in the first catalyst. In other examples, Zr is present in an amount of about 5.6 wt. % in the first catalyst.

The alumina catalyst can be regenerated as necessary under suitable conditions for the processes described herein. Consistent with some aspects of the subject matter, the alumina catalyst is regenerated in-situ in air. The alumina catalyst can be regenerated at a temperature of 400° C. to 600° C. For example, the alumina catalyst can be regenerated at 500° C. Consistent with some aspects of the subject matter, the alumina catalyst is regenerated for 30 minutes to 3 hours. For example, the alumina catalyst is regenerated for 1 to 2 hours.

The second catalyst, can be 'regenerable' catalyst combinations for $C_2$-$C_5$ olefin conversion consist of doped zeolites such as crystalline silicates of the group ZSM-5 (MFI or BEA frameworks), CHA, FER, FAU, MWW, MOR, EUO, MFS, ZSM-48, MTT or TON having Si/Al higher than 10, or a dealuminated crystalline silicate of the group ZSM5 (MFI or BEA frameworks), CHA, FER, FAU, MWW, MOR, EUO, MFS, ZSM-48, MTT or TON having Si/Al higher than 10, or a phosphorus and/or boron modified crystalline silicate of the group ZSM-5 (MFI or BEA frameworks), CHA, FER, FAU, MWW, MOR, EUO, MFS, ZSM-48, MTT or TON having Si/Al higher than 10, or molecular sieves of the type silico-aluminophosphate of the group AEL. Additional additives for mixing with the doped zeolites in the second catalyst consist of SiO2, MgO, or metathesis catalysts (i.e. (tungstated or molybdenum doped alumina, zirconia, or SiO2 supports.

The second catalyst comprises a doped or undoped zeolite catalyst and/or a doped or undoped W—Zr catalyst. In many instances, the second catalyst is a doped or undoped zeolite catalyst. For example, the second catalyst can be a doped ZSM-5 zeolite catalyst. The doped ZSM-5 zeolite catalyst can include boron, phosphorus, or both. For example the doped ZSM-5 catalyst can include boron and phosphorus. In another example, the doped ZSM-5 catalyst can include boron. The second catalyst can further comprise $\gamma$-alumina catalyst, W—SiO$_2$ catalyst, or W—Zr catalyst, and wherein the $\gamma$-alumina optionally includes Zr, W, or Mo.

Boron and the phosphorus which are present in an amount of from 2 wt. % to 5 wt. % of the second catalyst. In some instances, boron is present in an amount of about 2.5 wt. % and phosphorus is present in an amount of about 3.7 wt. % of the second catalyst. In some examples, boron is present in an amount of from 2 wt. % to 5 wt. % of the second catalyst. For example, boron is present in an amount of 3.5 wt. % to 4.1 wt. % of the second catalyst.

In some instances, the second catalyst comprises an undoped ZSM-5 zeolite catalyst. The second catalyst comprising the undoped ZSM-5 zeolite catalyst can further comprise Mo—Zr catalyst or W—Zr catalyst.

The $C_2$-$C_7$ olefins formed from the process described herein have a mass yield of at least 65%. In many examples, the mass yield is at least 70%. The mass yield of the one or more $C_2$-$C_7$ olefins is from 65% to 98%. For example, the mass yield of the one or more $C_2$-$C_7$ olefins is from 75% to 95%. In some cases, the mass yield of the one or more $C_2$-$C_7$ olefins is from 70% to 99%. In some examples, the mass yield of the one or more $C_2$-$C_7$ olefins is from 80% to 95%.

The present disclosure also provides a process for converting ethanol to one or more $C_2$-$C_7$ olefins, the process comprising: contacting a first stream comprising the ethanol with a first catalyst in a first reactor at a temperature of about 360° C., gauge pressure of 0 bar, and a WHSV of about 2.1, wherein the first catalyst comprises a $\gamma$-alumina catalyst including Zr, to form a second stream; and contacting the second stream with a second catalyst in a second reactor at a temperature from 340° C. to 400° C., gauge pressure of 0 bar, and a WHSV of about 2.1, wherein the second catalyst comprises a doped ZSM-5 zeolite catalyst, wherein the doped zeolite catalyst includes boron, phosphorus, or both and forming the one or more $C_2$-$C_7$ olefins in a mass yield from 80% to 95%.

Also provided is a process for converting ethanol to one or more $C_2$-$C_7$ olefins, the process comprising: contacting a first stream comprising the ethanol with a first catalyst in a first reactor at a temperature of about 360° C., gauge pressure of about 0 bar, and a WHSV of about 2.1, wherein the first catalyst comprises a $\gamma$-alumina catalyst including Zr, to form a second stream; separating a portion of water from the second stream; and contacting the second stream with a second catalyst in a second reactor at a temperature from 380° C. to 410° C., gauge pressure of about 0 bar, and a WHSV of about 2.1, wherein the second reactor comprises a boron doped ZSM-5 zeolite catalyst and forming the one or more $C_2$-$C_7$ olefins in a mass yield from 80% to 95%.

The present disclosure further provides a process for converting ethanol to one or more $C_2$-$C_7$ olefins, the process comprising: contacting a first stream comprising the ethanol with a first catalyst in a reactor at a temperature from 330° C. to 360° C., gauge pressure of about 0 bar, and a WHSV from 2.1 to 2.3, wherein the first catalyst comprises a $\gamma$-alumina catalyst including Zr, to form a second stream; and contacting the second stream with a second catalyst in the reactor at the same temperature, pressure, and WHSV as the first reactor, wherein the second catalyst comprises an undoped ZSM-5 zeolite catalyst and a W—Zr catalyst or Mo—Zr catalyst and forming the one or more $C_2$-$C_7$ olefins in a mass yield from 81% to 99%.

EXAMPLES

Reactor Set-Up

Ethanol conversion to $C_3$-$C_7$ olefins was carried out at 300-500° C., via fixed bed reactors, containing specified catalyst(s), and flowing preheated (160° C.) vaporized ethanol in a downward flow over the fixed catalyst bed while co-feeding nitrogen at atmospheric pressure or under moderate gauge pressures (i.e. 0-30 bar). The flow rate of ethanol was controlled by Teledyne Model 500D syringe pumps, and the flow rates were adjusted to obtain the targeted olefin WHSV (weight hourly space velocity). The internal reaction temperature was maintained constant via a Lindberg Blue M furnace as manufactured by Thermo-Scientific. Ethanol conversion and selectivity was calculated by analysis of the liquid phase reactor effluent by GC (gas chromatography) for organic and water content, and online GC analysis of non-condensed hydrocarbons (i.e. $C_2$-$C_7$ olefins) relative to nitrogen as internal standard. Thus, passing a vaporized stream of fuel grade ethanol over silicated, zirconated, titanated or fluorinated alumina followed by passing the hydrous ethylene over the second fixed bed catalyst at between 350-450° C. provides the ethanol refiner with the ability to produce $C_2$-$C_7$ olefins in high yields.

The following representative examples relate to converting fuel grade or hydrous ethanol to primarily propylene and butenes in >75% yields along with lesser amounts of $C_{5+}$ olefins and aromatics (BTX—benzene, toluene, xylene) via a single unit operation at >60% ethylene conversion along with quantitative ethanol conversion. Unreacted ethylene may be separated and recycled. Ethylene conversion may be increased, by increasing temperature in the second reactor, but higher ethylene conversions in some cases results in higher levels of aromatics which are more economically unfavorable as compared to higher yields to $C_3$-$C_7$ olefins which may be converted to renewable diesel fuel. Conversely, ethylene conversion may be decreased (~40%) resulting in higher selectivity/yield to $C_3$-$C_7$ olefins (~90%), lesser yield to aromatics, and higher levels of ethylene recycle.

Catalyst Preparation Example 1a

Impregnated Zr- $\gamma$-Alumina (nominal Zr metal 5 wt. %) Catalyst preparation: Zr- $\gamma$-alumina catalyst was prepared by incipient wetness technique as described. The precursor metal salts (Sigma Aldrich): 2.64 g zirconium (IV) oxynitrate hydrate was dissolved in deionized water (14.9 ml). Upon salt dissolution, the solution was added in dropwise fashion to 15 g $\gamma$-alumina support. The resulting mixed metal oxide was manually mixed to assure complete wetting, and the resulting impregnated catalyst was dried at 160° C. for 1 hr, and afterwards calcined at 500° C. for 4 hrs.

Catalyst Preparation Example 1b

Impregnated W- $\gamma$-Alumina (nominal W metal 15 wt. %) Catalyst Preparation: W- $\gamma$-alumina catalyst was prepared by incipient wetness technique as described. The precursor metal salts (Sigma Aldrich): 1.74 g ammonium tungstate pentahydrate hydrate was dissolved in deionized water (9.2 ml). Upon salt dissolution, the solution was added in dropwise fashion to 8 g γ-alumina support. The poor solubility of ammonium tungstate salt in water required multiple water dissolutions and additions of the tungstate salt to the γ-alumina support to achieve the required tungstate loading. After each water/salt addition, the resulting mixed metal oxide was manually mixed to assure complete wetting after each tungstate salt addition, and the resulting impregnated catalyst was dried at 160° C. for 1 hr, and afterwards calcined at 500° C. for 4 hrs.

Catalyst Preparation Example 1c

Impregnated boron and phosphor impregnated ZSM-5 zeolite catalyst preparation: boron and phosphor impregnated zeolite catalyst was prepared by incipient wetness technique as described. 0.83 g phosphoric acid (85%) and 0.94 g boric acid was dissolved in deionized water (7.2 ml). Upon dissolution, the solution was added in dropwise fashion to 6 g ZSM-5 zeolite support (i.e. Zeolyst type CBV-5524 H$^+$). The resulting impregnated catalyst was dried at 160° C. for 1 hr, and afterwards calcined at 550° C. for 3 hrs.

Example 2

Two-Stage reactor configuration without removal of water from ethanol dehydration: Reaction Conditions: T=360° C. in first reactor, T=340° C. in second reactor WHSV=2.1 (ethanol basis), P=0 bar; Catalysts zirconated (5.6 wt. %) γ-alumina in first reactor and boron/phosphorus doped ZSM-5 zeolite (2.5 wt. % boron/3.7 wt. % phosphorus) admixed with Zr-alumina (5.6 wt. % Zr) in second reactor.

| Reactor Effluent Composition - Wt. % of Total: | |
| --- | --- |
| Ethylene | 30 |
| Propylene | 13 |
| Butenes | 27 |
| $C_5$ olefins | 14 |
| $C_2$-$C_4$ saturates | 7 |
| Aromatics | 5 |
| $C_{6+}$ olefins | 4 |

Ethylene conversion ~62%; mass yield to $C_3$-$C_7$ olefins based on ethylene conversion ~81%; mass yield to aromatics based on ethylene conversion ~8%.

Example 3

Two-Stage reactor configuration without removal of water from ethanol dehydration: Reaction Conditions: T=360° C. in first reactor, T=370° C. in second reactor WHSV=2.1 (ethanol basis), P=0 bar; Catalysts zirconated (5.6 wt. %) γ-alumina in first reactor and boron/phosphorus doped ZSM-5 zeolite (2.5 wt. % boron/3.7 wt. % phosphorus) admixed with γ-alumina in second reactor.

| Reactor Effluent Composition - Wt. % of Total: | |
| --- | --- |
| Ethylene | 24 |
| Propylene | 15 |
| Butenes | 30 |
| $C_5$ olefins | 11 |
| $C_2$-$C_4$ saturates | 9 |
| Aromatics | 7 |
| $C_{6+}$ olefins | 4 |

Ethylene conversion ~70%; mass yield to $C_3$-$C_7$ olefins based on ethylene conversion ~76%; mass yield to aromatics based on ethylene conversion ~10%.

Example 4

Two-Stage reactor configuration without removal of water from ethanol dehydration: Reaction Conditions: T=360° C. in first reactor, T=380° C. in second reactor WHSV=2.1 (ethanol basis), P=0 bar; Catalysts zirconated (5.6 wt. %) γ-alumina in first reactor and boron/phosphorus doped ZSM-5 zeolite (2.5 wt. % boron/3.7 wt. % phosphorus) admixed with W—SiO$_2$ (W ~15 wt. %) in second reactor.

| Reactor Effluent Composition - Wt. % of Total: | |
| --- | --- |
| Ethylene | 39 |
| Propylene | 17 |
| Butenes | 24 |
| $C_5$ olefins | 14 |
| $C_2$-$C_4$ saturates | 4 |
| Aromatics | 1 |
| $C_{6+}$ olefins | 1 |

Ethylene conversion ~40%; mass yield to $C_3$-$C_7$ olefins based on ethylene conversion ~90%; mass yield to aromatics based on ethylene conversion ~4%.

Example 5

Two-Stage reactor configuration without removal of water from ethanol dehydration: Reaction Conditions: T=360° C. in first reactor, T=395° C. in second reactor WHSV=2.1 (ethanol basis), P=0 bar; Catalysts zirconated (5.6 wt. %) γ-alumina in first reactor and boron/phosphorus doped ZSM-5 zeolite (2.5 wt. % boron/3.7 wt. % phosphorus) in second reactor.

| Reactor Effluent Composition - Wt. % of Total: | |
| --- | --- |
| Ethylene | 22 |
| Propylene | 17 |
| Butenes | 29 |
| $C_5$ olefins | 16 |
| $C_2$-$C_4$ saturates | 8 |
| Aromatics | 6 |
| $C_{6+}$ olefins | 2 |

Ethylene conversion ~70%; mass yield to $C_3$-$C_7$ olefins based on ethylene conversion ~82%; mass yield to aromatics based on ethylene conversion ~8%.

Example 6

Two-Stage reactor configuration with removal of water from ethanol dehydration: Reaction Conditions: T=360° C. in first reactor, T=410° C. in second reactor WHSV=2.1 (ethanol basis), P=0 bar; Catalysts zirconated (5.6 wt. %) γ-alumina in first reactor and boron doped ZSM-5 zeolite (4.1 wt. % boron) in second reactor in second reactor.

| Reactor Effluent Composition - Wt. % of Total: | |
|---|---|
| Ethylene | 30 |
| Propylene | 19 |
| Butenes | 24 |
| $C_5$ olefins | 15 |
| $C_2$-$C_4$ saturates | 7 |
| Aromatics | 3 |
| $C_{6+}$ olefins | 2 |

Ethylene conversion ~55%; mass yield to $C_3$-$C_7$ olefins based on ethylene conversion ~85%; mass yield to aromatics based on ethylene conversion ~6%.

Example 7

Two-Stage reactor configuration with removal of water from ethanol dehydration: Reaction Conditions: T=360° C. in first reactor, T=410° C. in second reactor WHSV=2.1 (ethanol basis), P=0 bar; Catalysts zirconated (5.6 wt. %) γ-alumina in first reactor and boron doped ZSM-5 zeolite (3.7 wt. % boron) admixed with W-zirconium (W ~15 wt. %) in second reactor.

| Reactor Effluent Composition - Wt. % of Total: | |
|---|---|
| Ethylene | 32 |
| Propylene | 13 |
| Butenes | 26 |
| $C_5$ olefins | 18 |
| $C_2$-$C_4$ saturates | 6 |
| Aromatics | 3 |
| $C_{6+}$ olefins | 2 |

Ethylene conversion ~60%; mass yield to $C_3$-$C_7$ olefins based on ethylene conversion ~88%; mass yield to aromatics based on ethylene conversion ~4%.

Example 8

Two-Stage reactor configuration with removal of water from ethanol dehydration: Reaction Conditions: T=360° C. in first reactor, T=380° C. in second reactor WHSV=2.1 (ethanol basis), P=0 bar; Catalysts zirconated (5.6 wt. %) γ-alumina in first reactor and boron doped ZSM-5 zeolite (3.5 wt. % boron) admixed with Mo-alumina (W ~15 wt. %) in second reactor.

| Reactor Effluent Composition - Wt. % of Total: | |
|---|---|
| Ethylene | 44 |
| Propylene | 12 |
| Butenes | 22 |
| $C_5$ olefins | 15 |
| $C_2$-$C_4$ saturates | 6 |
| Aromatics | 0.5 |
| $C_{6+}$ olefins | 0.5 |

Ethylene conversion ~45%; mass yield to $C_3$-$C_7$ olefins based on ethylene conversion ~87%; mass yield to aromatics based on ethylene conversion ~2%.

Example 9

Single Stage reactor configuration: Reaction Conditions: T=355° C. in reactor, WHSV=2.1 (ethanol basis), P=0 bar; Catalysts zirconated (5.6 wt. %) γ-alumina in first catalyst bed and Mo-zirconium (Mo ~15 wt. %) admixed with ZSM-5 zeolite in second catalyst bed.

| Reactor Effluent Composition - Wt. % of Total: | |
|---|---|
| Ethylene | 29 |
| Propylene | 16 |
| Butenes | 21 |
| $C_5$ olefins | 11 |
| $C_2$-$C_4$ saturates | 9 |
| Aromatics | 10 |
| $C_{6+}$ olefins | 4 |

Ethylene conversion ~60%; mass yield to $C_3$-$C_7$ olefins based on ethylene conversion ~75%; mass yield to aromatics based on ethylene conversion ~18%.

Example 10

Reaction Conditions: T=350° C., WHSV=2.3; First Catalyst Bed-zirconated γ-alumina (2.9 g); Second catalyst bed tungstated zirconium (1.7 g) admixed with ZSM5 zeolite (0.3 g); Feed Fuel Grade Ethanol (1% water)

| Reactor Effluent Composition - Wt %: | |
|---|---|
| Vapor phase | 78% |
| Mixed Butenes | 39% |
| Propylene | 33% |
| Ethylene | 18% |
| $C_5$ olefins | 9% |
| Other 'lights' | 1% |
| Organic liquid phase | 22% |
| Toluene | 22% |
| Ethyl Benzene | 6% |
| Xylenes | 32% |
| C9 Aromatics | 17% |
| Others | 23% |

Example 11

Reaction Conditions: T=330° C., WHSV=2.3; First Catalyst Bed zirconated γ-alumina (2.9 g); Second catalyst bed-tungstated zirconium (1.7 g) admixed with ZSM5 zeolite (0.3 g); Feed Fuel Grade Ethanol (1% water)

| Reactor Effluent Composition - Wt %: | |
|---|---|
| Vapor phase | 90% |
| Mixed Butenes | 26% |
| Propylene | 18% |
| Ethylene | 44% |
| $C_5$ olefins | 11% |
| Other 'lights' | 1% |
| Organic liquid phase | 10% |
| Toluene | 10% |
| Ethyl Benzene | 4% |
| Xylenes | 26% |
| C9 Aromatics | 31% |
| Others | 29% |

Example 12

Two-Stage reactor wherein the first reactor comprises a first catalyst: zirconated γ-alumina (2.9 g); Fuel Grade Ethanol feed rate=0.14 ml/min; T=360° C.; P=atm; the second reactor comprises a second catalyst: boron doped ZSM5 Zeolite (2.5 g); Water feed=0.02 ml/min; T=400° C.: P=atm.

| Reactor Effluent Composition - Wt. % of Total: | |
|---|---|
| Vapor Phase | |
| Ethylene | 31.61 |
| Propylene | 19.61 |
| Butenes | 25.37 |
| $C_5$ olefins | 15.95 |
| Ethane | 0.99 |
| Propane | 2.36 |
| Butane | 4.11 |

Prophetic Example 13

Two-Stage reactor configuration without removal of water from ethanol dehydration: Reaction Conditions: T=360° C. in first reactor, T=400° C. in second reactor WHSV=2.1 (ethanol basis), P=1 bar; Catalysts zirconated (4 wt. %) γ-Alumina in first reactor and boron/phosphorus doped ZSM-5 zeolite (4 wt. % boron/2 wt. % phosphorus) admixed with W—$SiO_2$ (W ~15 wt. %) in second reactor.

| Reactor Effluent Composition - Wt. % of Total: | |
|---|---|
| Ethylene | 39 |
| Propylene | 17 |
| Butenes | 24 |
| $C_5$ olefins | 14 |
| $C_2$-$C_4$ saturates | 4 |
| Aromatics | 1 |
| $C_{6+}$ olefins | 1 |

Ethylene conversion ~50%; mass yield to $C_3$-$C_7$ olefins based on ethylene conversion ~92%; mass yield to aromatics based on ethylene conversion ~3%.

Prophetic Example 14

Two-Stage reactor configuration with removal of water from ethanol dehydration: Reaction Conditions: T=360° C. in first reactor, T=370° C. in second reactor WHSV=2.1 (ethanol basis), P=1 bar; Catalysts zirconated (4 wt. %) γ-alumina in first reactor and boron doped ZSM-5 zeolite (4 wt. % boron) admixed with W-zirconium (W ~15 wt. %) in second reactor.

| Reactor Effluent Composition - Wt. % of Total: | |
|---|---|
| Ethylene | 32 |
| Propylene | 13 |
| Butenes | 26 |
| $C_5$ olefins | 18 |
| $C_2$-$C_4$ saturates | 6 |
| Aromatics | 3 |
| $C_{6+}$ olefins | 2 |

Ethylene conversion ~65%; mass yield to $C_3$-$C_7$ olefins based on ethylene conversion ~89%; mass yield to aromatics based on ethylene conversion ~4%.

Prophetic Example 15

Single Stage reactor configuration: Reaction Conditions: T=355° C. in reactor, WHSV=2.1 (ethanol basis), P=1 bar; Catalysts zirconated (5.6 wt. %) γ-alumina in first catalyst bed and Mo-zirconium (Mo ~15 wt. %) admixed with ZSM-5 zeolite in second catalyst bed.

| Reactor Effluent Composition - Wt. % of Total: | |
|---|---|
| Ethylene | 29 |
| Propylene | 16 |
| Butenes | 21 |
| $C_5$ olefins | 11 |
| $C_2$-$C_4$ saturates | 9 |
| Aromatics | 10 |
| $C_{6+}$ olefins | 4 |

Ethylene conversion ~60%; mass yield to $C_3$-$C_7$ olefins based on ethylene conversion ~80%; mass yield to aromatics based on ethylene conversion ~15%.

The following specific examples are intended to be illustrative of the invention and should not be construed as limiting the scope of the invention as defined by appended claims.

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A process for converting one or more $C_2$-$C_5$ linear or branched alcohols to one or more $C_2$-$C_7$ olefins, the process comprising:
    contacting a first stream comprising the $C_2$-$C_5$ linear or branched alcohols with a first catalyst in a first reactor at a temperature from about 200° C. to about 500° C., gauge pressure from 0 to about 30 bar, and a weight hourly space velocity (WHSV) of at least 0.5 to form a second stream, wherein the first catalyst comprises an alumina catalyst including, in neutral or ionic form, one or more of silicon (Si), zirconium (Zr), titanium (Ti), niobium (Nb), tungsten (W), or fluorine (F); and
    contacting the second stream with a second catalyst in a second reactor at a temperature from about 200° ° C. to about 500° C., gauge pressure from 0 to about 30 bar, and a WHSV of at least 0.5, wherein the second catalyst comprises a doped or undoped zeolite catalyst, thereby forming the one or more $C_2$-$C_7$ olefins in a mass yield of at least 65%.

2. The process of claim 1, wherein the one or more $C_2$-$C_5$ linear or branched alcohols is ethanol, propanol, butanol, or a combination thereof.

3. The process of claim 1, wherein the one or more $C_2$-$C_5$ linear or branched alcohols are bio-based and produced by fermentative processes.

4. The process of claim 1, wherein the one or more $C_2$-$C_5$ linear or branched alcohols are not derived from petroleum.

5. The process of claim 1, wherein the one or more $C_2$-$C_7$ olefins includes ethylene, propylene, butenes, $C_5$-$C_6$ olefins, one or more $C_2$-$C_6$ olefins, or a combination thereof.

6. The process of claim 1, wherein the alumina catalyst is a γ-alumina catalyst.

7. The process of claim 1, wherein the second catalyst further comprises a γ-alumina catalyst or a W—SiO$_2$ catalyst, and wherein the γ-alumina catalyst optionally includes Zr, W, or molybdenum (Mo).

8. A process for converting ethanol to one or more $C_2$-$C_7$ olefins, the process comprising:
   contacting a first stream comprising the ethanol with a first catalyst in a first reactor at a temperature of about 360° C., gauge pressure of 0 bar, and a weight hourly space velocity (WHSV) of about 2.1 to form a second stream, wherein the first catalyst comprises a γ-alumina catalyst including zirconium (Zr); and
   contacting the second stream with a second catalyst in a second reactor at a temperature from about 340° ° C. to about 400° C., gauge pressure of 0 bar, and a WHSV of about 2.1, wherein the second catalyst comprises a doped ZSM-5 zeolite catalyst that includes boron and phosphorus, thereby forming the one or more $C_2$-$C_7$ olefins in a mass yield from about 80% to about 95%.

9. The process of claim 1, further comprising:
   separating a portion of water from the second stream.

10. The process of claim 8, further comprising:
    separating a portion of water from the second stream.

11. The process of claim 8, wherein the boron and phosphorus are each present in an amount of less than 5 wt. % of the second catalyst.

12. The process of claim 8, wherein the boron and phosphorus are each present in an amount of from 2 wt. % to 5 wt. % of the second catalyst.

13. The process of claim 1, wherein the boron and phosphorus are each present in an amount of less than 5 wt. % of the second catalyst.

14. A process for converting one or more $C_2$-$C_5$ linear or branched alcohols to one or more $C_2$-$C_7$ olefins, the process comprising:
    contacting a first stream comprising the $C_2$-$C_5$ linear or branched alcohols with a first catalyst in a reactor at a temperature from about 200° ° C. to about 500° C., gauge pressure from 0 to about 30 bar, and a weight hourly space velocity (WHSV) of at least 0.5 to form a second stream, wherein the first catalyst comprises an alumina catalyst; and
    contacting the second stream with a second catalyst in the reactor, wherein the second catalyst comprises a doped zeolite catalyst that includes boron and phosphorus, thereby forming the one or more $C_2$-$C_7$ olefins.

15. The process of claim 14, wherein the one or more $C_2$-$C_5$ linear or branched alcohols is ethanol, propanol, butanol, or a combination thereof.

16. The process of claim 14, wherein the one or more $C_2$-$C_5$ linear or branched alcohols are bio-based and produced by fermentative processes.

17. The process of claim 14, wherein the one or more $C_2$-$C_5$ linear or branched alcohols are not derived from petroleum.

18. The process of claim 14, wherein the one or more $C_2$-$C_7$ olefins includes ethylene, propylene, butenes, $C_5$-$C_6$ olefins, one or more $C_2$-$C_6$ olefins, or a combination thereof.

19. The process of claim 14, wherein the first catalyst comprises a γ-alumina catalyst.

20. The process of claim 15, wherein the boron and the phosphorus are each present in an amount of less than 5 wt. % of the second catalyst.

21. The process of claim 15, wherein the boron and the phosphorus are each present in an amount from 2 wt. % to 5 wt. % of the second catalyst.

22. A process for converting one or more $C_2$-$C_5$ linear or branched alcohols to one or more $C_2$-$C_7$ olefins, the process comprising:
    contacting a stream comprising the $C_2$-$C_5$ linear or branched alcohols with at least two catalysts in a reactor at a temperature from about 200° C. to about 500° C., gauge pressure from 0 to about 30 bar, and a weight hourly space velocity (WHSV) of at least 0.5 to form the one or more $C_2$-$C_7$ olefins, wherein the at least two catalyst comprises an alumina catalyst and a doped zeolite catalyst, the doped zeolite comprising boron and phosphorus.

* * * * *

UNITED STATES PATENT AND TRADEMARK OFFICE
CERTIFICATE OF CORRECTION

| | | |
|---|---|---|
| PATENT NO. | : 12,043,587 B2 | Page 1 of 1 |
| APPLICATION NO. | : 17/695993 | |
| DATED | : July 23, 2024 | |
| INVENTOR(S) | : Jonathan Smith and Madeline Sjodin | |

It is certified that error appears in the above-identified patent and that said Letters Patent is hereby corrected as shown below:

In the Specification

At Column 1, Line 11, delete "Apr. 8, 2021," and insert -- Sep. 29, 2020, --

In the Claims

At Column 16, Claim 1, Line 51, delete "200° ° C." and insert -- 200° C. --

At Column 17, Claim 8, Line 16, delete "340° ° C." and insert -- 340° C. --

At Column 17, Claim 14, Line 40, delete "200° ° C." and insert -- 200° C. --

Signed and Sealed this
Twenty-fourth Day of September, 2024

Katherine Kelly Vidal
*Director of the United States Patent and Trademark Office*